United States Patent [19]

Huber et al.

[11] 4,008,963
[45] Feb. 22, 1977

[54] METHOD OF AND DEVICE FOR THE ANALYSIS OF SAMPLES BY MEANS OF FLAMELESS ATOMIC ABSORPTION SPECTROSCOPY

[75] Inventors: Bernhard Werner Huber, Uberlingen; Rolf Günther Arnold Tamm, Salem, both of Germany

[73] Assignee: Bodenseewerk Perkin-Elmer & Co. GmbH, Uberlingen, Germany

[22] Filed: Mar. 6, 1975

[21] Appl. No.: 555,723

[30] Foreign Application Priority Data

Mar. 7, 1974 Germany .......................... 2410892

[52] U.S. Cl. .................................. 356/85; 356/36
[51] Int. Cl.$^2$ ......................................... G01J 3/42
[58] Field of Search ........................... 356/36, 85–87

[56] References Cited

UNITED STATES PATENTS

| | | | |
|---|---|---|---|
| 3,419,359 | 12/1968 | Anderson | 356/87 |
| 3,832,060 | 8/1974 | Dahlquist | 356/85 |

OTHER PUBLICATIONS

Hauser, et al., *Analytical Chemistry* vol. 44, No. 11, Sept. 1972, pp. 1819–1821.
*Advances in Automated Analysis, Technicon International Congress,* 1969, vol. II, Mediad, Inc., N.Y., 1970, pp. 315–320.

*Primary Examiner*—Edward S. Bauer
*Assistant Examiner*—F. L. Evans
*Attorney, Agent, or Firm*—S. A. Giarratana; F. L. Masselle

[57] ABSTRACT

A method of atomization of a sample for analysis by atomic absorption spectroscopy in which the sample is progressively heated to drying, ashing and atomization temperatures by subjecting it sequentially to discrete ambient temperature increments.

A preferred form of apparatus for carrying out the method takes the form of a graphite fabric conveyor belt which carries the sample substance and travels transversely through three hollow cylindrical graphite tubes disposed in spaced justaposition with longitudinal axes parallel. The belt passes through each tube in sequence, by way of pairs of aligned longitudinal slots in the sidewalls of the tubes, the slots defining a common chordal plane of the tubes. Each tube is maintained, respectively in the direction of belt travel, at drying, ashing and atomization temperature for the particular sample. The tubes are heated by an electrical current of appropriate magnitude passed between pairs of electrodes associated with the ends of the tubes. A beam of radiation of selected spectral characteristics is passed axially through the last tube to a detector which determines the degree of absorption of the radiation beam by the atomized sample in that tube.

14 Claims, 3 Drawing Figures

METHOD OF AND DEVICE FOR THE ANALYSIS OF SAMPLES BY MEANS OF FLAMELESS ATOMIC ABSORPTION SPECTROSCOPY

BACKGROUND OF THE INVENTION

1. Field of the Invention

This invention relates generally to atomic absorption spectroscopy and more particularly to the flameless atomization of samples preparatory to analysis by means of atomic absorption spectroscopy.

2. Description of the Prior Art

While the atomization of samples for atomic absorption spectroscopy initially was accomplished by spraying a finely nebulized sample into a flame, at the present time, a substantial proportion of AA spectroscopic analysis employs what is referred to as flameless atomization in apparatus frequently referred to as a graphite furnace. Such a furnace most commonly takes the form of a single graphite tube mounted between two annular electrodes. A sample is inserted at or near the midpoint of the tube's length and the tube is heated by an electric current passed between the electrodes.

The current supply and, therefore, the degree of heating takes place in accordance with a specific program. Initially, a relatively small current is passed through the tube raising the temperature to the value required for drying of the sample, i.e., to evaporate a solvent, for example. Thereafter, the temperature of the tube is raised to the point required for thermal decomposition of the sample molecule, known as "ashing". Finally, a very high current is supplied raising the temperature of the tube to the point where atomization takes place so that the elements contained in the sample are present in an atomic state, forming an atomic cloud within the graphite tube.

A beam of radiation from a source of known spectral characteristics is passed axially through the tube to a detector. The source, customarily a hollow cathode lamp, is selected to produce radiation of a relatively narrow band of wavelengths corresponding to the resonance lines of the element sought to be detected. This radiation is absorbed by the atomic cloud in proportion to the concentration of the element in question, the degree of absorption being measured by the detector. In order to prevent combustion of the graphite tube at the high operating temperature involved, it is enveloped in a flowing stream of protective gas. For additional information regarding conventional graphite furnace-type sample cells, reference may be had to U.S. Pat. Nos. 3,778,156 and 3,788,752.

In a graphite furnace of the type described, the rate at which samples can be processed is limited to the thermal lag, i.e., the length of time required for the tube to heat from drying to ashing or ashing to atomization temperature after the heating current is increased. This delay limits the number of analyses which can be carried out in a given period of time.

Another drawback of prior apparatus is the fact that a reproducible measurement of signal peaks requires exact observation of the temperature and flow conditions extant during the analysis. The reason for this is that there is some absorption of the radiation beam and a concomitant output signal from the detector, if the atomic cloud is formed in the graphite tube while it is heating up to atomizing temperature. In addition, the atomic cloud is partially dispersed by diffusion and the protective gas stream flowing through the sample tube and this tends to decrease the detector output signal level. These spurious effects obviously interfere with the determination of the true output signal representing the concentration of the element being analyzed for.

Still another disadvantage of prior art devices is the fact that a separate sample is required for each element sought to be determined. In other words, a single sample cannot be subjected to analysis for two different elements. Consequently, it is necessary to subject duplicate samples to drying, ashing and decomposition; and it is also necessary to change the spectral light source after one analysis is completed to substitute the appropriate source for the second element.

With the foregoing state of the art in view, it is the primary general object of the invention to overcome or at least mitigate the problems and shortcomings outlined above.

A more specific overall object of the invention is to provide a novel method and apparatus which materially increases the rate at which sample analysis can be accomplished by means of flameless atomic absorption spectroscopy.

A further object is the provision of an improved method and apparatus for atomization of a sample for atomic absorption spectroscopic analysis which enables determination of more than one element from a single sample.

Another object is to provide a novel method and apparatus for flameless AA sample atomization in which the atomic cloud is present in the analysis beam for a relatively longer time and at a relatively more constant volume and density than in comparable prior art devices.

To the accomplishment of the foregoing and other objectives, the invention contemplates a method of atomization of a sample for atomic absorption spectroscopic analysis in which the sample is subjected sequentially to discrete ambient temperature increments to effect, in distinct, progressive stages, drying, ashing and atomization.

In one of its preferred forms, the apparatus for carrying out the foregoing method may comprise a plurality of chambers disposed in proximity to one another and a conveyor for transporting the sample to be analyzed in sequence to each of such chambers. The chambers are heated to respective predetermined temperatures, the chamber which is lattermost in the sequence being heated to the temperature required to effect atomization of the sample. This lattermost chamber has a radiation transparent passage through which a beam of radiation of selected spectral characteristics is passed to a detector arrangement for determining the degree of absorption of the beam by the atomized sample.

DESCRIPTION OF THE PREFERRED EMBODIMENT

Figure 1:
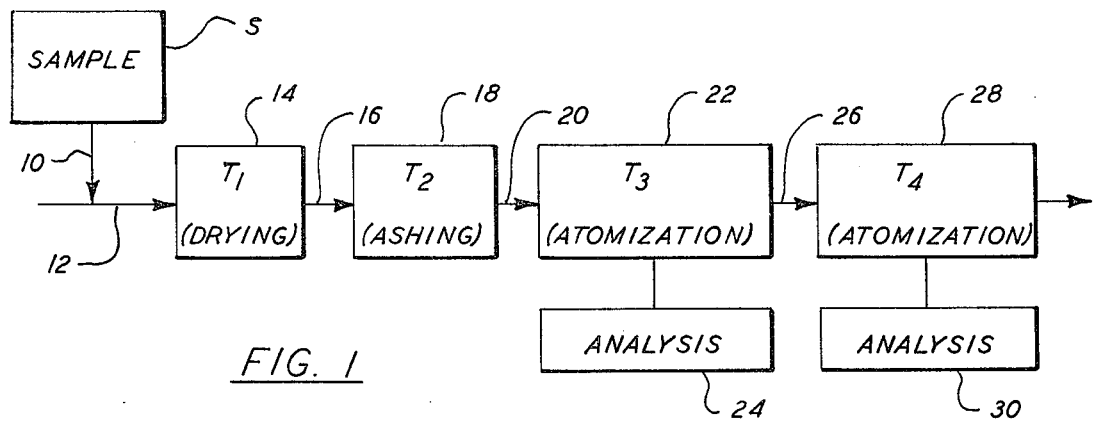
FIG. 1 is a flow diagram depicting the method contemplated by the present invention.

Referring first to FIG. 1 which shows a flow diagram of the method contemplated by the invention, block S represents a supply of a sample to be subjected to analysis. As indicated by arrows 10 and 12, the sample is conveyed to a station 14 which is maintained at a temperature $T_1$ appropriate to drying the particular sample being analyzed. The sample moves continuously through drying station 14 and then, as indicated by arrow 16, passes through an ashing station 18 which is maintained at a substantially constant temperature $T_2$, the value of which is selected to achieve ashing of the sample. The sample moves continuously through station 18 and as indicated by arrow 20, passes through an atomization station 22 maintained at a substantially constant temperature $T_3$ of a magnitude such as will effect atomization of the sample during its transit time through the station.

As indicated by block 24, the atomized sample in station 22 is subjected to spectrophotometric analysis as by passing a beam of radiation through the atomized sample to a suitable detector, in a manner well known in the art and previously mentioned. At this juncture, it should be understood that the apparatus for actual atomic absorption spectrophotometric analysis as a practical matter would not consist simply of a spectral radiation source and detector; however, as the actual analytical instrument and the various specific forms it may take are well known in the art and are not germane to the present invention, a further description is unnecessary. For additional details as to the structure and operation of AA analytical instruments, reference may be had to U.S. Pat. Nos. 2,847,899 and 3,137,758.

Unless it is desired to analyze a sample for two or more elements, the process is complete at station 22. Assuming that the sample is to be analyzed for an additional element, the sample passes from station 22, as indicated by arrow 26, to a second atomizing station 28 which is maintained at a temperature $T_4$ appropriate to achieving atomization of the additional element. Obviously, the value of temperature $T_4$ exceeds $T_3$ and, for that matter, each of the stations in the sequence of the process is at a temperature higher than the station which proceeds it in the order of sample movement.

While the sample is at station 28, a second spectrophotometric analysis, as indicated by block 30, is performed by passing a second beam of radiation through the atomized sample to a detector, as previously explained. However, the radiation beam employed at station 28 would have a different spectral characteristic than that at 22, being selected to have a relatively narrow band of wavelengths corresponding to the resonance lines of the additional element sought to be detected.

In connection with the method just described, it is important to note that the sample is supplied continuously for a finite period of time, a period long enough to ensure that sample is passing through station 22 and, if present, station 28, continuously during the time the sample is being subjected to analysis. In this way, an equilibrium is obtained between the losses of sample substance occurring by diffusion or carried off by the flow of protective gas required at this station as will be seen presently in conjuction with a description of particular apparatus for carrying out the process. In this way, the retention time of the atomic cloud which is very brief in conventional apparatus, is relatively prolonged thus enhancing both the accuracy and the reproducibility of analytical results.

As will be seen in the ensuing description of apparatus for carrying out the method, the sample may be conveyed between stations on an endless belt, in which case it is desirable that the method comprise the additional step of subjecting the belt exiting from the lattermost station (be it 22 or 28) to a suitable cleaning action before it is returned to the sample station S.

Figure 2:
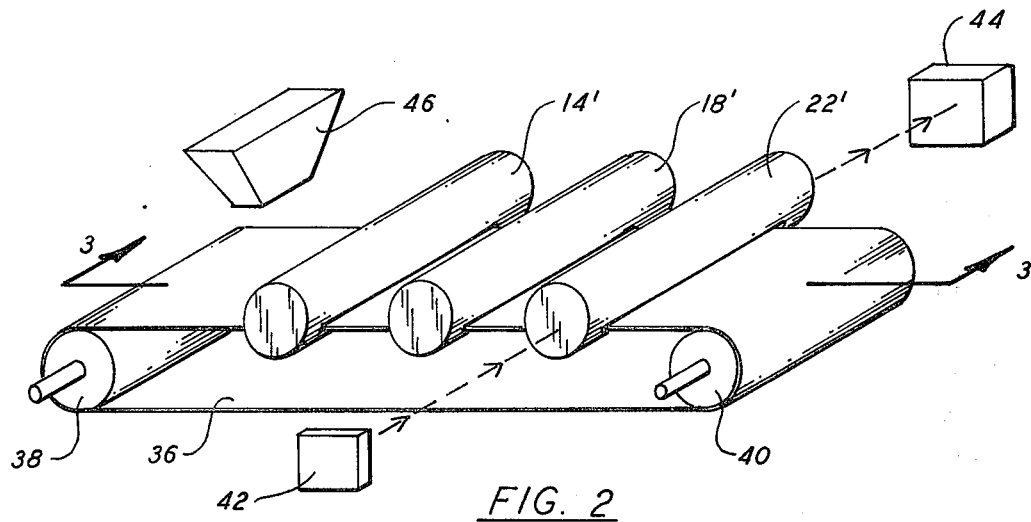
FIG. 2 is a schematic view in perspective elevation representing a preferred examplary embodiment of apparatus according to the present invention for atomizing a sample for AA spectroscopic analysis.
Figure 3:
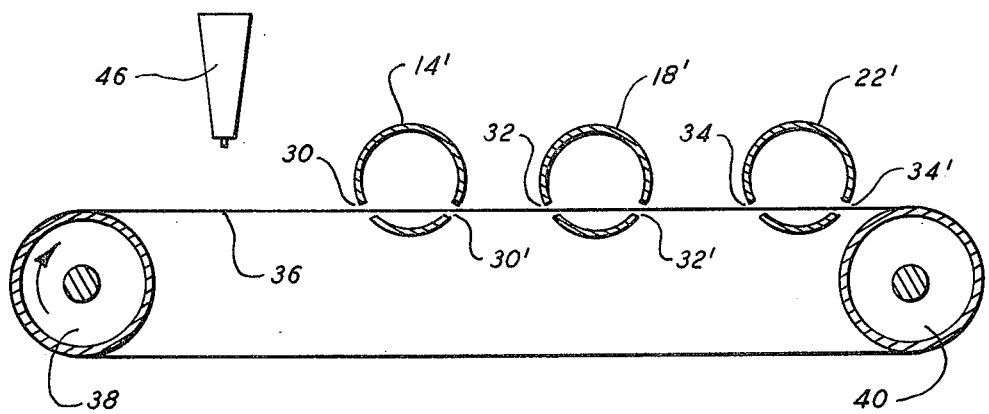
FIG. 3 is a sectional view on line 2—2 of FIG. 1 looking in the direction of the arrows.

Referring now to FIGS. 2 and 3, there is a diagramatically illustrated a preferred form of apparatus for carrying out the method described above. To simplify the description and to facilitate correlation between the method and apparatus, some common reference numerals, primed in the case of the apparatus, are employed in FIGS. 2 and 3. In the apparatus, each of the stations 14, 18 and 22 of FIG. 1 take the physical form of chambers defined by hollow tubular or cylindrical bodies 14', 18' or 22', two of which, viz., 14' and 18', have closed ends. For the sake of simplicity, no tubular body is shown in the apparatus corresponding to station 28 and it would, of course, be identical to 22'.

Tubular bodies 14', 18' and 22', which are preferably fabricated of graphite, are arranged in spaced juxtaposition with their longitudinal axes substantially parallel. Each of the bodies has a pair of aligned longitudinal slots, 30, 30'; 32, 32'; 34, 34', in its sidewalls which define a diametral or chordal plane through the body. For reasons which will become apparent as the description proceeds, the slots in tubular body 22' would normally define a chordal plane spaced at a substantial distance below (as viewed in FIG. 2) the longitudinal axis of the body. In the illustrated embodiment, the planes defined by the slots in all tubular bodies are chordal planes and are coincident.

An endless belt 36 of graphite fabric travels over graphite rollers 38 and 40 positioned so that the upper run of the belt passes through the aligned slots of tubular bodies 14', 18' and 22'.

Each of the hollow bodies is provided with means, not shown, for maintaining the body at a predetermined elevated temperature. Conveniently, this can be accomplished by passing an electrical current longitudinally through each of the tubular bodies by means of electrodes, not shown, contacting the ends of each body in the manner well known and previously described in connection with conventional graphite tube atomization apparatus. Body 14' is heated to a temperature of, for example, 212° F, sufficient for drying of a sample, i.e., evaporation of the solvent. Hollow body 18', the next following 14' in the direction of belt travel and sample transport, is maintained at ashing temperature, e.g., 1832° F, at which thermal decomposition of the sample under analysis takes place. Hollow body 22', lattermost in the direction of the belt travel, is heated to a temperature sufficient to effect atomization of the sample, e.g., 4564° F. In a configuration where two atomization chambers are employed, the lattermost would, of course, operate at a higher temperature than the one preceding it. Belt 36 is heated indirectly by passage through the chambers defined by tubes 14', 18' and 22'.

By having the ends of tube 22' open, or closed by a transparent material, a radiation transparent passage is formed extending through the chamber defined by the tube. In this connection, it is pointed out that the position of the slots in tubular body 22', at least, defines a chordal plane spaced well below the axial center of the tube, leaving the upper portion of the interior unobstructed. Accordingly, a radiation beam from a spectral source represented symbolically at 42 can pass centrally and axially through the hollow body without vignetting to a detector 44.

An applicator 46 is provided for supplying sample to the upper surface of conveyor belt 36.

In the preferred mode of operation, the belt moves continuously and sample is applied continuously for a finite period of time to the belt so that each sample occupies a lengthwise segment of the belt which exceeds the diameter of the tubes. The sample passes in sequence through the chambers defined by tubes 14', 18' and 22', the rate of passage being adjusted to allow the sample to attain the ambient temperature in the chamber. In this manner, the time for any given sample to pass through the tubes is relatively prolonged and, consequently, the atomic cloud is present in the chamber of tube 22' for a similarly prolonged period, thus enhancing both the accuracy and reproducibility of analytical results, as already explained.

However, it is possible to operate the apparatus in a discrete sample mode. In this case, a predetermined sample quantity is applied to the belt and the belt is advanced intermittently so that the sample is stationary in each of the tubes in sequence for a predetermined period of time before being transferred to the next chamber. Operated in this fashion, a peak-type signal is obtained from the detector as in conventional equipment.

Thus, the objects of the invention are fulfilled by the provision of methods and apparatus for flameless atomization of samples at a more rapid through-put rate and which permit analysis for plural elements from a single sample while facilitating reproducibility of analytical results.

What is claimed is:

1. Apparatus for flameless atomization of a sample for spectroscopic analysis comprising:
    means for defining a plurality of chambers disposed in proximity to one another;
    continuous conveyor means for transporting in sequence through each of said chambers a sample to be analyzed;
    means for heating said chambers to respective predetermined temperatures, each higher than in the preceding chamber in the direction of sample transport, one of said chambers being heated to a temperature required for drying the sample, another of said chambers in the direction of sample transport being heated to a temperature required for ashing the sample, and one of said chambers lattermost in the sequence being heated to the temperature required to effect atomization of the sample; and
    means defining a radiation-transparent passage through said lattermost chamber.

2. Apparatus for atomic absorption spectroscopic analysis of a sample comprising flameless atomization apparatus according to claim 1 in combination with:
    means for passing a beam of radiation of selected spectral characteristics through the radiation-transparent passage of the lattermost chamber and concomitantly through the atomized sample therein; and
    means for detecting the degree of absorption of said radiation beam by said sample.

3. The combination defined in claim 2 further comprising:
    means defining a radiation-transparent passage through the penultimate chamber of the sequence;
    means for passing through the radiation transparent passage of the penultimate chamber a second beam of radiation having spectral characteristics different from the first beam; and
    means for detecting the degree of absorption of said second radiation beam.

4. Apparatus according to claim 1 wherein said chambers are of elongate configuration and disposed in spaced juxtaposition with their longitudinal axis in substantial parallelism.

5. Apparatus according to claim 4 wherein the sample transport means is a conveyor belt passing through said chambers transversely of the longitudinal axes via aligned slot apertures in the sidewalls of the chambers.

6. Apparatus according to claim 4 wherein said chambers are of tubular configuration and the slot apertures in each define a plane parallel to and spaced from the longitudinal axis of the chambers.

7. Apparatus according to claim 6 wherein said chambers are of hollow cylindrical configuration and said plane is a chordal plane.

8. Apparatus according to claim 7 wherein the chordal planes of all chambers are coincident.

9. Apparatus according to claim 8 wherein said conveyor belt is an endless belt of graphite fabric.

10. Apparatus according to claim 9 further comprising means positioned before the first of said chambers for depositing sample material onto said belt.

11. Apparatus according to claim 10 wherein said depositing means supplies to said belt a quantity of sample material having lengthwise extent in the direction of belt travel which exceeds the individual transverse dimension of at least the lattermost chamber.

12. In an apparatus for flameless atomization of a series of samples for spectroscopic analysis having means for defining a plurality of heating stations disposed in proximity to one another, continuous conveyor means for transporting in sequence through each of said heating stations samples to be analyzed and means for heating said heating stations to respective predetermined temperatures, a method of flameless atomization of samples for spectroscopic analysis which includes the steps of automatically transporting by means of said continuous conveyor means a discrete quantity of each of said samples in sequence, continuously, and at a substantially constant rate through said heating stations, while maintaining in each of said heating stations a respective temperature effective to produce, in the order of sample transport, drying, ashing and atomization of the samples.

13. A method according to claim 12 including the further step of subjecting the sample while in the atomization temperature station to spectrophotometric analysis.

14. A method according to claim 13 wherein said sample is continuously supplied to said atomization station during the spectrophotometric analysis at a rate sufficient to achieve equilibrium therein with respect to losses of the atomized samples.

* * * * *